(12) United States Patent
Kuwano et al.

(10) Patent No.: US 8,518,010 B2
(45) Date of Patent: Aug. 27, 2013

(54) DISPOSABLE ABSORBENT WEARING ARTICLE

(75) Inventors: Seiichi Kuwano, Kagawa (JP); Yoshio Ono, Kagawa (JP); Kyota Saito, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 288 days.

(21) Appl. No.: 12/935,706

(22) PCT Filed: Feb. 18, 2009

(86) PCT No.: PCT/JP2009/052813
§ 371 (c)(1),
(2), (4) Date: Dec. 6, 2010

(87) PCT Pub. No.: WO2009/122802
PCT Pub. Date: Oct. 8, 2009

(65) Prior Publication Data
US 2011/0071488 A1  Mar. 24, 2011

(30) Foreign Application Priority Data

Mar. 31, 2008 (JP) .................................. 2008-092712

(51) Int. Cl.
*A61F 13/20* (2006.01)
*A61F 13/15* (2006.01)

(52) U.S. Cl.
USPC .................................. 604/385.3; 604/385.29

(58) Field of Classification Search
USPC ............... 604/385.24–385.3, 385.22, 385.31, 604/393, 394, 396
See application file for complete search history.

(56) References Cited

U.S. PATENT DOCUMENTS

| | | | | |
|---|---|---|---|---|
| 6,478,786 B1 * | 11/2002 | Glaug et al. | ............. | 604/385.27 |
| 7,060,058 B2 | 6/2006 | Otsubo et al. | | |
| 2004/0010241 A1 * | 1/2004 | Sanders et al. | ........... | 604/385.24 |
| 2004/0243085 A1 * | 12/2004 | Veith et al. | ................. | 604/385.3 |
| 2005/0107763 A1 | 5/2005 | Matsuda et al. | | |

FOREIGN PATENT DOCUMENTS

| | | |
|---|---|---|
| JP | 1992-32718 | 3/1992 |
| JP | 05-031135 | 2/1993 |
| JP | 2000-288017 | 10/2000 |
| JP | 2002-306534 | 10/2002 |
| JP | 2004-236832 | 8/2004 |
| JP | 2005-270359 | 10/2005 |
| JP | 2006-525858 | 11/2006 |
| JP | 2007-509725 | 4/2007 |
| WO | WO 2004/105665 | 12/2004 |

* cited by examiner

*Primary Examiner* — Jackie Ho
*Assistant Examiner* — Peter S Vasat
(74) *Attorney, Agent, or Firm* — Brinks Hofer Gilson & Lione

(57) ABSTRACT

A disposable absorbent wearing article having an absorbent chassis and an annular elasticized waist panel. The elastic waist panel includes a front waist panel and a rear waist panel. A rear waist panel has a dimension in a longitudinal direction that is greater than that of the front waist panel and further includes a first elasticized region, a second elasticized region defining a waist band and a third elasticized region located toward a crotch region of the article. Tensile stress of the third elasticized region, as measured in a transverse direction, is less than the tensile stress of the first and second elasticized regions.

19 Claims, 8 Drawing Sheets

DISPOSABLE ABSORBENT WEARING ARTICLE

TECHNICAL FIELD

The present invention relates to disposable absorbent wearing articles and more particularly to disposable diapers for baby and/or adult, toilet-training pants for baby, incontinent briefs, sanitary napkins of pants-type and the other articles adapted to receive and to absorb body waste such as urine, feces and the other body waste.

RELATED ART

Such articles widely available may be classified into first, second and third types.

An example of the article classified into the first type has front and rear waist regions, and a crotch region extending between these two waist regions so as to have opposite outlines curved inward as viewed in a transverse direction wherein the article comprises inner and outer sheets forming together a cover (chassis) adapted to cover the wearer's lower torso and an absorbent core sandwiched between these inner and outer sheets. In such article of the first type, the front and rear waist regions and front as well as rear waist bands contiguous to these waist regions are elasticized to be circumferentially contractile along the waist line of the chassis. In a similar manner, respective side flaps extending outward from opposite side edges of the crotch region of the chassis are elasticized along respective side edges thereof (i.e., gasket cuffs) so as to be circumferentially contractile around the wearer's legs.

An example of the article classified into the second type comprises a chassis (i.e., outer sheet) substantially the same as said chassis of the article classified into the first type in shape as well in size and a separately prepared liquid-absorbent structure (referred to also as an absorbent inner) provided at least in the crotch region of the chassis and including an absorbent core therein. In such article of the second type also, desired regions of the chassis are elasticized to be contractible just as the chassis in the article of the first type.

An example of the article classified into the third type comprises an annular waist panel formed by front and rear waist panels each having a relatively large width and extending in the transverse direction and a separately prepared liquid-absorbent structure (referred to hereinafter as absorbent chassis) connected between the front and rear waist panels and including an absorbent core therein. In such article of the third type also, desired regions at least of the chassis are elasticized to be contractible just as the chassis of the article classified into the first type.

Each of these articles of the first, second and third types may be optionally provided with barrier leg-cuffs extending in the longitudinal direction along opposite side edges of the absorbent core or of the absorbent structure and having elasticized free edges.

The article of the first, second and third types can be classified roughly into the articles of so-called open-type having the front and rear waist regions not joined to each other along the transversely opposite side edges thereof and the articles of so-called pull-on-type having the front and rear waist regions previously joined to each other along the transversely opposite side edges thereof. Figuratively, the articles of the first and second types have concave shape curved inwardly while the article of the third type is substantially side toppling H-shaped as viewed when these articles are developed in both the longitudinal direction and the transverse direction.

Typically, it is possible for the article of pull-on-type (referred to hereinafter simply as pull-on-article or pull-on-diaper) to be high speed mass-produced at a relatively low cost by use of "method of laterally oriented feeding mode".

The term "pull-on-article" used herein refers to the diaper having a waist-opening as well as a pair of leg-openings previously defined so that the wearer's legs may be inserted into the diaper through the waist-opening and leg-openings and the diaper is pulled up along the wearer's waist to put the diaper on the wearer's body.

As used herein, the term "a method of laterally oriented feeding mode" means a method advantageously employed to make the pull-on-article. In view of the fact that the pull-on-type article has its front and rear waist regions previously joined to each other along the respective opposite side edges, the component materials of the article are fed in a machine direction so that individual completed articles being adjacent one to another may be oriented in a cross direction orthogonal to the machine direction. In this way, the component materials can be achieved and thereby the articles can be mass-produced at a high speed.

The articles of the first, second and third types exploited as the pull-on-articles are suitable for mass-production at a low cost by the "method of laterally oriented feeding mode". This is for the reason that, for the pull-on-type article, elastic elements adapted to elasticize the front and rear waist region as well as peripheral edges surrounding the wearer's legs so as to be contractible may be linearly fed and arranged in the machine direction. However, it should be appreciated that, so far as the articles of the first and second types, the elastic elements adapted to elasticize the peripheral edges of the leg-openings are fed in the machine direction so as to describe sine curves undulating in the transverse direction (e.g., See JP 1993-31135 T). While these leg elastic elements may be construed as a whole to be fed in the machine direction, it is doubtless that these elastic elements are attached to describe the sine curve-like line and respective segments (i.e., a plurality of longitudinally divided segments of respective lines along which these elastic elements are attached) undesirably present unevenness in a stretch ratio. As an adverse effect of such uneven stretch ratio, for example, irregular gathers or frills appear in the side flaps of the chassis under contraction of the leg elastic elements or the side flaps are curled inward or outward in the vicinity of those irregular gathers or frills. In consequence, not only the article put on the wearer's body may be disfigured but also fitness of the article around the wearer's thighs and/or inguinal region may become uneven and may cause leak of body waste.

In the case of the articles classified into the first and second types, the chassis comprises a sheet material having a sufficiently large area to cover desired regions of the wearer's lower torso. However, use of the sheet material having such relatively large area may result in the article which is voluminous as a whole, particularly in the crotch region and the vicinity thereof when the article is put on the wearer's body. Such excessive bulkiness makes the article put on the wearer's body appear to be undesirably "baggy". The leg elastic elements are typically attached, by adhesive, to the side flaps defined by the portions of the chassis extending outward in the transverse direction from the opposite side edges of the absorbent core, the absorbent structure or the absorbent chassis. It should be noted here that the leg elastic elements are usually attached to the side flaps along lines sufficiently spaced inward from the outer edges thereof to prevent the adhesive from being exposed and adversely affecting the wearer's skin. Consequentially, the side flaps partially extend outward in the transverse direction from the lines defined by the elastic element and the side flaps are formed with relatively large and uneven gathers or frills. Depending on how the user looks at it and/or depending on what the user prefers, the side flaps having such gathers or frills often present "not neat" appearance of the article when it is put on the wearer's body.

In the case of the article classified into the third type, in view of the fact none of sheet materials having relatively large area is required for the respective component members such as the front and rear waist panels and the absorbent chassis, on one hand, and from a viewpoint of respective geometries thereof, the article is able to present in many cases rather "neat" or "sporty" appearance when it is put on the wearer's body. Such article presenting "neat" or "sporty" impression can be put on the body without any hesitation. Obviously, it should not be construed that all the articles of the third type present such desirable "neat" or "sporty" appearance.

One example of the article classified into the third type is found in the disclosure of JP2006-525858T. JP2006-525858T discloses a garment in the form of the pull-on-type article (i.e., disposable diaper). This garment comprises an absorbent structure (i.e., absorbent chassis) extending in the longitudinal direction and an annular elastic waist panel extending in the transverse direction and joined to front and rear ends of the absorbent chassis.

The absorbent chassis comprises, in turn, a topsheet, a backsheet and an absorbent core sandwiched between these sheets. The absorbent chassis further includes side flaps respectively extending outward in the transverse direction from opposite side edges of the absorbent chassis and a pair of barrier leg cuffs provided aside inward from the respective side flaps so as to rise above the topsheet when the diaper is put on the wearer's body. Laterally outer regions of the respective side flaps and free side edges of the respective barrier leg cuffs are elasticized to be contractible by associated elastic elements attached to these regions so as to extend in the longitudinal direction.

The annular elastic waist panel comprises a front waist panel and a rear waist panel joined to each other by seams arranged respective opposite side edges of the respective panels. The front and rear waist panels respectively include elasticized waist band regions, lateral elasticized regions contiguously to inner sides of the respective elasticized waist band regions and opposed to and spaced from each other in the transverse direction, and non-elasticized regions extending between the respective lateral elasticized regions. The elasticized waist band regions and the lateral elasticized regions are elasticized to be contractible by a plurality of elastic elements attached to these regions so as to extend in the transverse direction (circumferential direction around the waist). The respective non-elasticized regions are provided on inner surfaces thereof with patches printed with graphics adapted to be looked therethrough from the exterior.
PATENT DOCUMENT 1: JP 2006-525858 T

DISCLOSURE OF THE INVENTION

Problem to be Solved by the Invention

The article of the third type according to the invention disclosed by JP2006-525858T is claimed to be distinguished from the articles of the first and second types in that this article does not use the absorbent chassis having a relatively large area to cover a substantially entire area of the desired regions of the wearer's lower torso. However, it is required for the absorbent chassis to have a substantially the same degree of the absorbing capacity as the absorbent region or the absorbent structure including the absorbent core in the articles of the first and second types. To meet this requirement, it is inevitable for the absorbent core included by the absorbent chassis to have the relatively large width as in the articles of the first and second types. Consequentially, the crotch region of the article is squeezed between the wearer's thighs and undesirably deformed, resulting in creating a feeling of discomfort against the wearer or causing leak of body waste.

Despite such inevitable requirement, JP2006-525858T neither teaches nor suggests any means for effective solution of such problem. If the chassis having a relatively large area is not used as claimed, this invention should find an effective means to prevent potential leak of body waste.

In view of the problem susceptible to occur in the front and rear waist panels, particularly in the deformable rear waist panel along its lateral regions when the article is put on the wearer's body as has been described above, it is an object of the present invention to provide an absorbent wearing article improved to present "neat" or "sporty" and aesthetic appearance on the wearer's body and additionally to prevent leak of body waste effectively.

The other objects of the present invention will be apparent from the following description of specific embodiments of the invention.

Measure to Solve the Problem

The present invention relates to an improvement in a disposable absorbent wearing article comprising a longitudinal center line and a transverse center line, a front waist region, a rear waist region and a crotch region, an elasticized front waist panel and an elasticized rear waist panel respectively defining the front waist region and the rear waist region and an absorbent chassis defining respective parts of the front and rear waist regions and the crotch region and joined to the front waist panel and to the rear waist panel.

The improvement according to the present invention comprises features as follow: the absorbent chassis comprises an absorbent structure including an absorbent core and a pair of side flaps extending outward in the transverse direction from lateral regions of the absorbent core. Each of the pair of side flaps is elasticized to be elastically contractible under the effect of at least single strand-like elastic element attached thereto so as to extend in the longitudinal direction. The front waist panel comprises a first elasticized region and a second elasticized region lying adjacent to the first elasticized region so as to define a waist band. The rear waist panel comprises a third elasticized region corresponding to the first elasticized region, a fourth elasticized region corresponding to the second elasticized region and fifth elasticized region lying adjacent to the third elasticized region so as to extend aside toward the side of the crotch region. The third elasticized region and the fourth elasticized region are elasticized by a plurality of strand-like elastic elements extending in the transverse direction. The fifth elasticized region has inner side edges opposed to each other in the transverse direction and obliquely extending so as to intersect with the longitudinal center line and is elasticized by at least a single strand-like elastic element to be elastically contractible. Tensile stress of the fifth elasticized region in the transverse direction is set to be lower than those of the first through fourth elasticized regions. A dimension of the rear waist panel as measured in the longitudinal direction is larger than that of the front waist panel as measured in the longitudinal direction by that of the fifth elasticized region.

The present invention includes preferred embodiments as follow.

A line defined by the elastic element nearest to the crotch region in the third elasticized region, a line defined by the outermost elastic element in each of the side flaps as viewed in the transverse direction and the inner edge of the fifth elasticized region cooperate together to form an imaginary triangle in each of the lateral regions opposed in the transverse direction.

The first and second elasticized regions cooperating together to form the front waist region is elasticized by a plurality of strand-like elastic elements extending in the transverse direction to be elastically contractible.

The inner side edges of the fifth elasticized region are concavely curved inward so as to describe circular arcs.

The at least single strand-like elastic element in the fifth elasticized region extends short of the inner side edges.

Side edges opposite in the transverse direction of the front waist panel are joined to side edges opposed in the transverse direction of the rear waist panel to form an annular waist panel having a waist-opening and a pair of leg-openings.

Effect of the Invention

The disposable absorbent wearing article according to the present invention can reliably achieve the expected purpose of solving the problem susceptible to occur in the front and rear waist panels, particularly in the easily deformable lateral regions of the rear waist panel when the article is put on the wearer's body so that the article may present "neat" or "sporty" and aesthetic appearance and prevent leak of body waste.

The other effects of the invention as well as advantages obtained by embodiments thereof will be apparent from the detailed description given hereunder.

Figure 1:
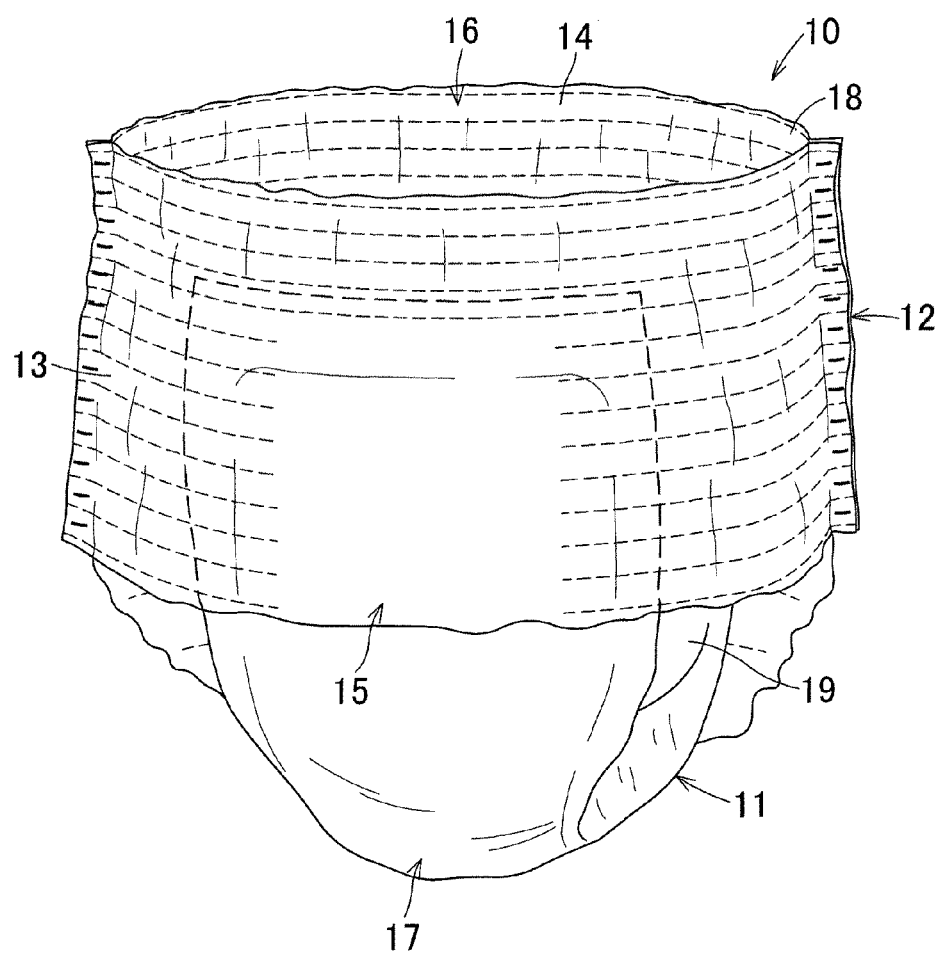
[FIG. 1] Perspective view of a disposable absorbent wearing article according to the present invention.

IDENTIFICATION OF REFERENCE NUMERALS USED IN THE DRAWINGS 10 disposable absorbent wearing article
11 absorbent chassis
12 annular elasticized waist panel
12A front waist panel
12B rear waist panel
20 absorbent structure
23a absorbent core
31 side flap
33 elastic element
36 deformation guide
37 auxiliary elastic element
40 first elasticized region
42 second elasticized region
43 first elastic element
44 second elastic element
45 third elasticized region
46 fourth elasticized region
47 fifth elasticized region
47A imaginary triangular region
49 third elastic element
50 fourth elastic element
51 fifth elastic element

DETAILED DESCRIPTION OF THE PREFERRED EMBODIMENTS

As will be apparent from FIGS. 1 and 2, the present invention will be described based on a pull-on-type diaper 10 as one example of the article according to the present invention. The diaper 10 has a longitudinal center line L1 and a transverse center line L2. It should be appreciated that these denotations L1 and L2 will be eliminated in the following description.

While the present invention is applicable to the diaper of both the pull-on-type and the open-type, it will be preferable to exploit the invention in the pull-on-type rather than in the open-type. In other words, while the diaper of open-type is not excluded from the applicability of the present invention, the disclosure thereof will be exclusively based on the diaper of pull-on-type (referred to hereinafter simply as pull-on diaper).

As used herein, the term "diaper of open-type" refers to the diaper with its the front and rear waist regions adapted to be joined along respective opposite side edges by fastening means such as mechanical fasteners to cover the lower torso of the wearer first when the diaper is actually put on the wearer's body.

The diaper 10 is of the previously described third type and basically comprises an absorbent chassis 11 and an annular elasticized waist panel 12. The diaper 10 has an outer surface 13, an inner surface 14 opposed to the outer surface 13, a front waist region 15, a rear waist region 16, a crotch region 17 extending between these front and rear waist regions 15, 16, a waist-opening 18 and a pair of leg-openings 19. The waist-opening 18 is defined by the annular elasticized waist panel 12 and a pair of leg-openings 19 is defined by the absorbent chassis 11 and the annular elastic waist panel 12.

The absorbent chassis 11 presents a longitudinally longer rectangular shape contoured by opposite side edges 11a extending in the longitudinal direction and opposite ends 11b, 11c extending in the transverse direction. The absorbent chassis 11 has front and rear end regions 11d, 11e partially defining the front and rear waist regions 15, 16, respectively, and an intermediate region 11f extending between these end regions 11d, 11e so as to define the crotch region 17.

Figure 4:
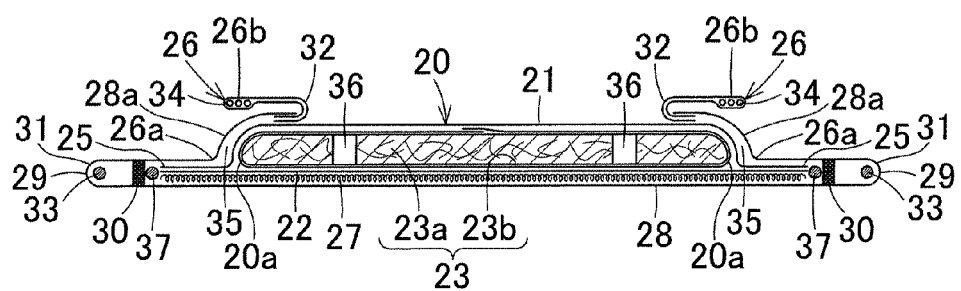
[FIG. 4] Schematic sectional view taken along the line IV-IV in FIG. 2.
Figure 5:
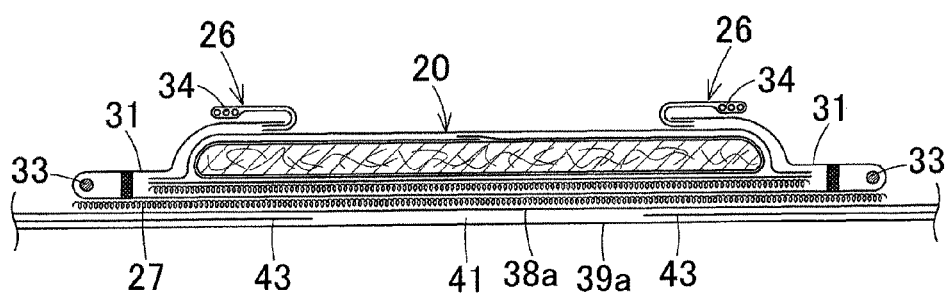
[FIG. 5] Schematic sectional view taken along the line V-V in FIG. 2.

Referring to FIGS. 4 and 5, the absorbent chassis 11 includes an absorbent structure 20. The absorbent structure 20 comprises a liquid-pervious liner facing the wearer's skin (i.e., topsheet) 21, a liquid-impervious backsheet 22, and an absorbent panel 23 formed by an absorbent core 23a having a sufficient capacity to absorb bodily fluids and a liquid-dispersant sheet 23b wrapping the absorbent core 23a. The absorbent chassis 11 further comprises a pair of end flaps 24 (See FIG. 2) formed by portions of the liner 21 facing the wearer's skin and the backsheet 22 extending outward in the transverse direction from the absorbent structure 20 at its end regions, a pair of inner side flaps 25 formed by portions of the liner 21 facing the wearer's skin and the backsheet 22 extending in the longitudinal direction along the opposite side edges of the absorbent structure 20 and optionally a pair of barrier leg cuffs 26 extending in the longitudinal direction adjacently to the opposite lateral regions 20a of the absorbent structure 20.

Along the pair of end flaps 24 and the pair of inner side flaps 25, a portion of the liner 21 facing the wearer's skin and the backsheet 22 opposed to this portion of the liner 21, the liner 21 facing the wearer's skin and the surface of the absorbent panel 23 opposed to this liner 21, the backsheet 22 and the surface of the absorbent panel 23 opposed to this backsheet 22, and the peripheral edge of the liner 21 facing the wearer's skin and the peripheral edge of the backsheet 22 opposed to each other are respectively bonded by means of hot melt adhesive (not shown) coated in appropriate pattern such as a spiral pattern or stripe pattern.

The absorbent structure 20 further includes a first sheet member 28 attached to a bottom surface of the absorbent structure 20 by hot melt adhesive coated zone 27 and respective portions of this first sheet member 28 extending outward from the absorbent structure 20 in the transverse direction are folded back inward in the transverse direction. In the vicinity of respective folds 29, respective two layers of the first sheet member 28 partially folded back in this manner are bonded together by hot melt adhesive 30 to form a pair of sleeve-like outer side flaps 31. The respective outer side flaps 31 cover the outer side edges of the respective inner side flaps 25.

Each of the barrier leg cuffs 26 comprises a prolongation 28a of the first sheet member 28 extending from the associated outer side flap 31 and a second sheet member 32 joined to the prolongation 28a by suitable joint means such as hot melt adhesive (not shown). The barrier leg cuff 26 has a proximal edge 26a and a distal edge 26b. As shown in FIG. 2, longitudinal ends 26c of the free edge 26b are folded back so that the free edge 26b as a whole may be directed outward in the transverse direction and surfaces of the end 26c opposed to each other as a result of folding back are joined together by suitable joint such as hot melt adhesive (not shown). Though not illustrated, it is also possible to fold back and fix the respective ends 26b so that the distal edge 26b may be directed inward as viewed in the transverse direction, if it is desired.

When the respective barrier leg cuffs 26 are formed by a second sheet member 32 different from the first sheet member 28 as in the case of the illustrated embodiment, these cuffs 26 may be formed by material different from that of the respective outer side flaps 31 if it is necessary. However, it is possible to form these cuffs from the first sheet member 28 alone. In addition, it is also possible to form the respective barrier leg cuffs 26 from an independent sheet member, i.e., using neither the first sheet member 28 nor the second sheet member 32 and then to attach them to the absorbent structure 20 along its lateral zones, respectively.

If the respective barrier leg cuffs 26 are independently formed and attached to the absorbent structure 20 in this manner, an alternative arrangement may be contemplated wherein the respective inner side flaps 25 further extend outward in the transverse direction so that the cuffs 26 may be attached to the upper surfaces of these inner side flaps 25. Nonetheless, the illustrated embodiment according to which the respective outer side flaps 31 cover the respective inner side flaps 25 ensures practical benefits. Specifically, it is ensured to prevent the outer side edges (often defined by cut edges of the sheet) of the respective inner side flaps 25 from irritating the wearer's skin.

Figure 2:
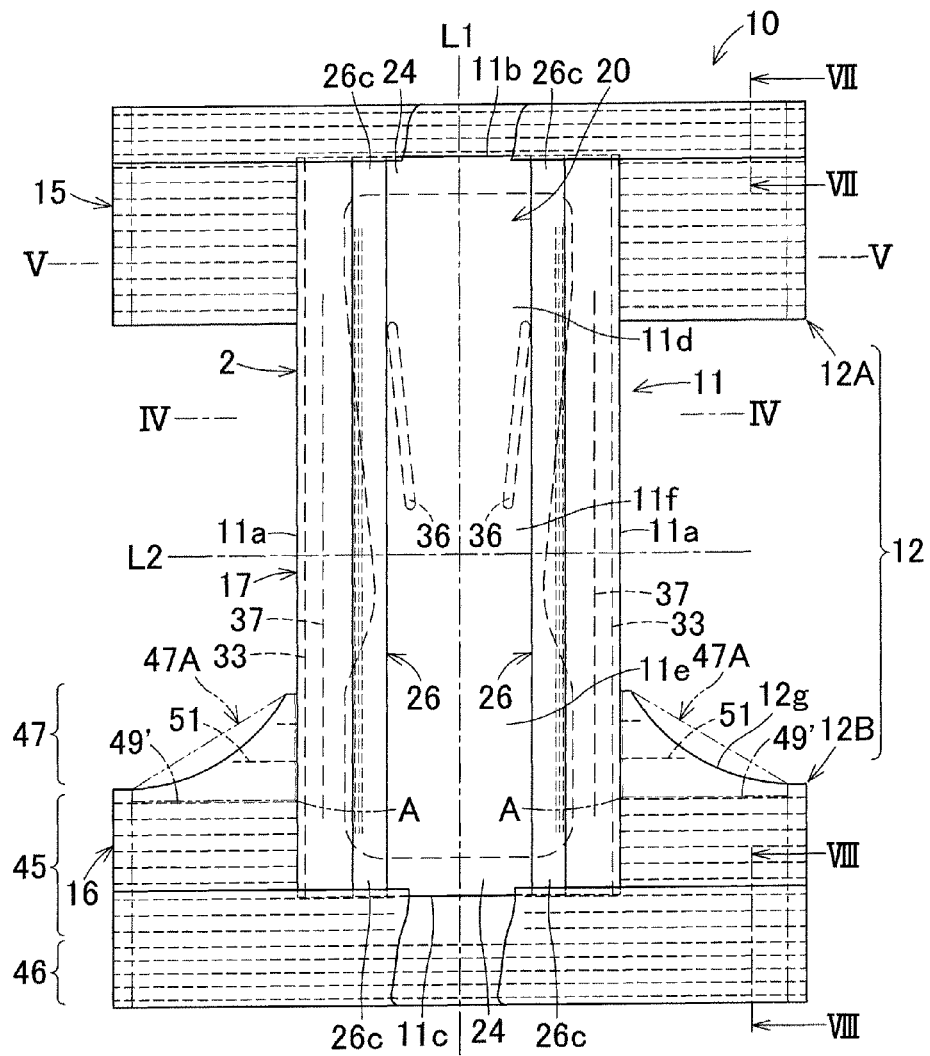
[FIG. 2] Partially cutaway plan view showing the article as viewed from its inner side with front and rear waist regions peeled off from each other along the seams along side edges of these waist regions followed by flatly developing these regions in the transverse direction as well as in the longitudinal direction.

Referring to FIGS. 2 and 4, the respective outer side flaps 31 are elasticized to be contractible by attaching strand-like elastic elements 33 under tension in the longitudinal direction within the sleeve-like structures thereof by hot melt adhesive (not shown). With the diaper put on the wearer's body, the respective outer side flaps 31 bows inward as viewed in the transverse direction under contraction of the elastic elements 33 and elastically pressed against the wearer's thighs. It should be appreciated that two or more elastic elements 33 may be provided for each of the outer side flaps 31, if desired.

In each of the barrier leg cuffs 26, the free edge 26b is elasticized to be contractible by attaching a plurality of strand-like elastic elements 34 under tension in the longitudinal direction within the sleeve-like structure of the folded back second sheet member 32 by hot melt adhesive (not shown). Alternatively, the single sheet being elastically contractible and having desired width may be used to form the distal edge 26b of each of the barrier leg cuffs 26 in stead of using a plurality of strand-like elastic elements 34.

Figure 6:
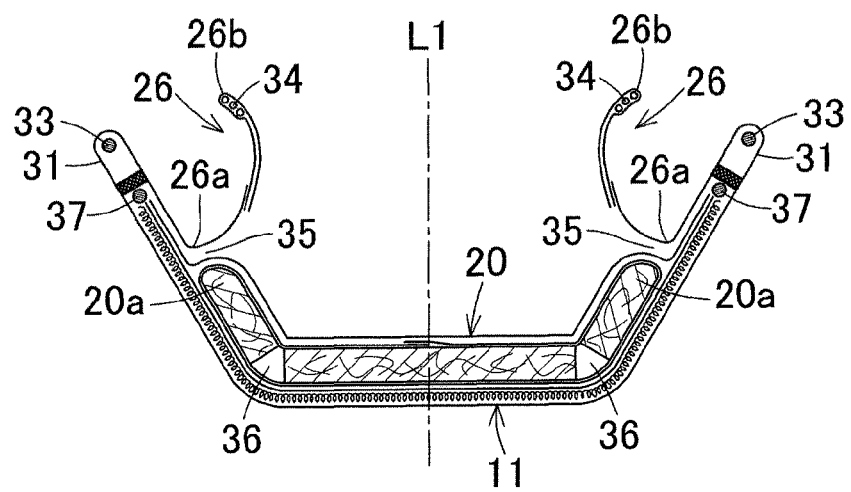
[FIG. 6] Schematic sectional view corresponding to FIG. 4 when the article is actually put on the wearer's body.

Now operation of the barrier leg cuff 26 will be described with reference to FIGS. 4 and 6. With the diaper put on the wearer's body, the free edge 26b and the vicinity thereof swing upward from the absorbent structure 20 toward the wearer's lower torso around a fulcrum line defined by the proximal edge 26a under contraction of the elastic elements 34. In this way, the distal edge 26b and the vicinity thereof are elastically pressed against the wearer's inguinal region and thighs in the vicinity of the inguinal region. While the respective proximal edges 26a are free from the elements or members (in the case of the illustrated embodiment, the transversely opposite side edges of the liner 21 facing the wearer's skin) facing the respective proximal edges 26a so far as the illustrated embodiment is concerned, the respective proximal edges 26a may be bonded to such elements or members, if desired. In both cases, pockets adapted to receive body waste are formed between the transversely opposite side edges of the absorbent structure 20 and the respective barrier leg cuffs 26. These pockets 35 cooperate with barriers against body waste defined by the respective distal edges 26b and the vicinity thereof swinging upward as has been described above to improve a capacity of the article to retain body waste.

Referring to FIGS. 2 and 4, the diaper 10 is formed in the crotch region 17 (corresponding to the intermediate region 11f) aside toward the front waist region 15 (corresponding to the front end region 11d of the absorbent chassis 11) of the diaper 10 with a pair of deformation guides 36 extending substantially in the longitudinal direction symmetrically about the longitudinal center line L1. More specifically, these deformation guides 36 are arranged so that the distance therebetween may be gradually reduced as these deformation guides 36 extend from the vicinity of the front waist region 15 toward the transverse center line L2. While this is one of preferred embodiments of the deformation guides 36, the present invention is not limited to such arrangement. For example, it is possible without departing from the scope of the invention to arrange the deformation guides 36 so as to extend in parallel to each other. As for the shape of cross section as well as the number of the deformation guides 36 also, there is no limitation. For example, each of the deformation guides 36 may have a V-shaped cross section and two or more guides may be formed on both sides of the longitudinal center line L1, respectively. In any case, the absorbent panel 23, eventually the lateral regions 20a of the absorbent structure 20 bow along the pair of deformation guides 36 and symmetrically about the longitudinal center line L1 toward the wearer's torso so as to face each other (See FIG. 6). The lateral regions 20a bowing in this manner define absorbent barriers adapted to come in close contact with the wearer's inguinal region or the vicinity thereof.

Outside in the transverse direction the opposite side edges of the absorbent panel 23, strand-like elastic elements serving to facilitate or assist deformation along the deformation guides 36 extend in the longitudinal direction under tension within the respective outer side flaps 31 and contractibly attached to the first sheet member 28 by hot melt adhesive (not shown) so that the respective elastic elements 37 may intersect elastic elements 43 for the elasticized front waist panel 12A to be hereinafter described in detail and may be interlinked therewith. In order to facilitate or assist deformation along the guides 36, it is also possible to arrange the elastic elements 37 further close to the absorbent panel 23.

The respective elastic elements 33, 37 are set to have a contractile force or a tensile stress substantially at the same level but lower than that of the respective elastic elements 34. It should be appreciated that the respective elastic elements 33 may be set to have a contractile force or a tensile stress higher than that of the respective elastic elements 37 as well as the elastic elements 34 or vice versa.

In the illustrated embodiment, the respective deformation guides 36 are exploited in slits extending through the absorbent core 23a in its thickness direction. According to a method for making the article of this type (disposable diaper), materials such as a mixture of short fibers, particles or powders are dispersed and accumulated in a mold by exerting a negative pressure on an air-permeable bottom wall of the mold (i.e., under a suction) to mold the absorbent core 23a. In this case, the air-permeable bottom wall of the mold may be provided with non-meshy (i.e., air-impervious) regions corresponding to the respective deformation guides 36 to form the slits along which none of the materials is accumulated.

The respective deformation guides 36 are not limited to such slits but the other various configurations may be selected. For example, it is possible to exploit these deformation guides 36 as linear regions along which a mass of the materials per unit area is lower than a mass of the materials per unit in the remaining region of the absorbent core 23a. In this alternative embodiment of the deformation guide, it is possible to employ a mold provided on its air-permeable bottom wall with an air-permeable salient appropriately protuberating in the depth direction of the mold. In this case, a thickness of the accumulated materials on this salient is smaller than that in the remaining region of the absorbent core 23a and a mass per unit area is correspondingly smaller. It is also possible to compress the respective regions corresponding to the deformation guides 36 under heating or without heating to form the respective deformation guides 36. In this case also, the mass of the deformation guide 36 per unit area is higher than in the remaining region of the absorbent core 23a.

Rather than forming the respective deformation guides 36 in the absorbent core 23a alone, it is also possible to form them in the absorbent core 23a, the liquid-dispersant sheet 23b and the liner 21 facing the wearer's skin laminated one upon another so as to integrate these members one with another. In this case, such laminate is preferably compressed under heating or without heating so that the respective deformation guides 36 may appear on the surface of the absorbent structure 20.

Stock material for the liner 21 facing the wearer's skin may be selected from the group consisting of a nonwoven fabric made of synthetic fibers having bodily fluid-pervious hydrophobic and/or hydrophilic nature, a porous plastic film and a laminate thereof, all of which have been widely used in the related technical field.

Stock material for the backsheet 22 may be selected from the group consisting of a plastic film which is resistant to permeation of bodily fluids but moisture-pervious, a hydrophobic fibrous nonwoven fabric and a laminate thereof, all of which have been widely used in the related technical field.

For the absorbent core 23a, a mixture of well known art consisting of wooden fluff pulp, super-absorbent polymer particles or fibers having an absorbing capacity of several ten times their own weight and optionally thermoplastic staple fibers is suitable as stock material. The absorbent core 23a is contoured to present a concave shape curved inwardly and appropriately compressed in its thickness direction in order to improve its shape retaining and liquid-absorbent/dispersant properties. Consequentially, the absorbent core 23a is often described to be rigid in comparison with the liner 21 facing the wearer's skin, the backsheet 22 and the first and second sheet members 28, 32, and called as semirigid.

As stock material for the first and second sheet members 28, 32, a hydrophobic fibrous nonwoven fabric, a plastic film or a laminate thereof, which is resistant to permeation of bodily fluids but moisture-pervious, all of which are well known in the related technical field is suitable.

Figure 3:
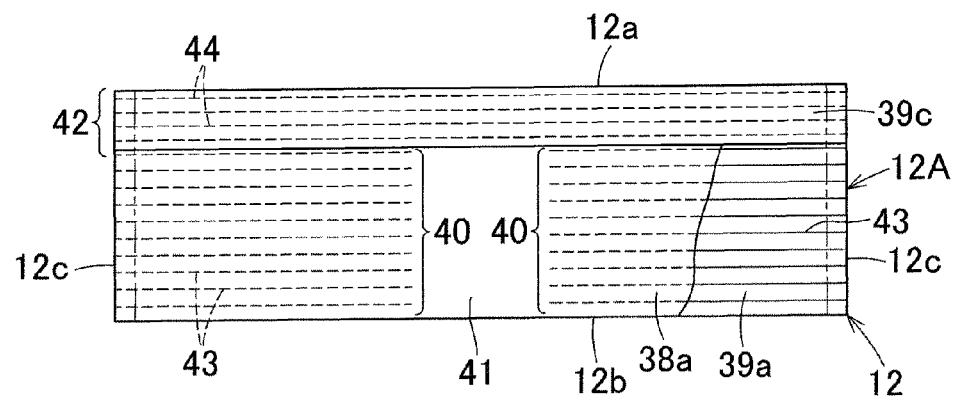
[FIG. 3] Partially cutaway plan view similar to FIG. 2 except that an absorbent chassis has been eliminated for convenience of illustration.
Figure 3:
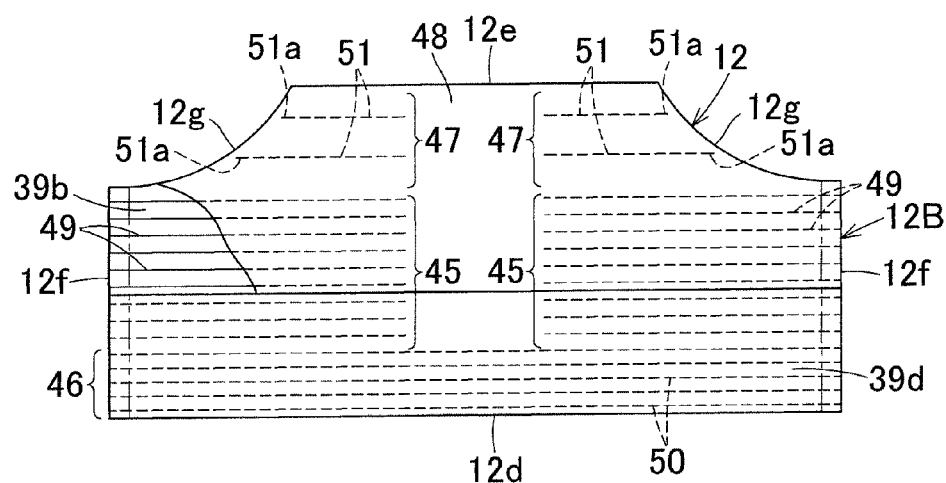

Referring to FIG. 3, the annular elastic waist panel 12 comprises the transversely longer rectangular front waist panel 12A contoured by an outer end 12a, an inner end 12b and transversely opposite side edges 12c and the substantially trapezoidal rear waist panel 12B contoured by an outer end 12d, an inner end 12e, transverse side edges 12f and transverse inner oblique side edges 12g. The rear waist panel 12B has a dimension in the longitudinal direction larger than the front waist panel 12A by a dimension of fifth elasticized region 47 to be described later in more detail. The respective inner oblique side edges 12g are preferably concavely curved inward so as to describe circular arcs, but those can also have a straight shape.

Figure 7:
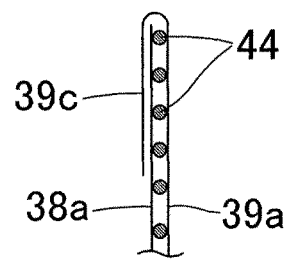
[FIG. 7] Schematic sectional view taken along the line VII-VII in FIG. 2.

The front waist panel 12A is formed by a laminate composed of an inner sheet 38a and an outer sheet 39a. The outer sheet 39a has a dimension in the longitudinal direction larger than that of the inner sheet 38a and a prolongation 39c thereof is folded back onto the inner sheet 38b (See FIG. 7) and bonded thereto by hot melt adhesive (not shown).

The front waist panel 12A has a pair of first elasticized regions 40 spaced from each other in the transverse direction and being contractible in the transverse direction, an optional first non-elasticized region 41 extending between the pair of first elasticized regions 40 and a second elasticized region 42 adjacent to the side of the paired first elasticized regions 40 close to the waist-opening 18 (i.e., upper edges of the respective first elasticized regions 40 as viewed in FIG. 3). The second elasticized region 42 defined a front waist band. The first and second elasticized regions 40, 42 are elasticized to be contractible in the transverse direction by attaching a plurality of strand-like first and second elastic elements 43, 44 under tension in the transverse direction between the inner and outer sheets 38a, 39a (See FIG. 5) by hot melt adhesive (not shown).

A pitch in the longitudinal direction at which the second elastic elements 44 are arranged is set to be smaller than a pitch in the same direction at which the first elastic elements 43 are arranged. Tensile stress of the second elasticized region 42 in the transverse direction is set to be higher than that of the respective first elasticized region 40.

The first non-elasticized region 41 lying in a middle of the front waist panel 12A as viewed in the transverse direction may be defined, for example, by the steps as follow: First, the paired first elasticized regions 40 are coated with hot melt adhesive in an appropriate pattern, leaving the first non-elasticized region 41 not coated with such adhesive, then continuous first elastic elements 43 are fed toward these respective regions so as to be fixed to the regions coated with the adhesive and these first elastic elements 43 are cut in the first non-elasticized region. Thereupon, the first elastic elements 43 automatically contract (snap back) since the first non-elasticized region 41 is not coated with the adhesive. In consequence, the first elastic elements 43 having a contractile force are no more substantially present in the first non-elasticized region 41. As used herein, the term "no more substantially present" suggests that extremely short end portions of the first elastic elements 43 having snapped back toward the respective first elasticized regions 40 may be left in this non-elasticized region 41. While such process of cutting is preferred, it is also possible to cut off the segments of the respective first elastic elements 43 extending over the first non-elasticized region 41 completely.

The steps to define the first non-elasticized region 41 are not limited to those as have been described above and can be defined by alternative steps different from those described above. For example, the segments of the first elastic elements 43 to extend across the first non-elasticized region 41 are placed without tension. In this case, the first non-elasticized region 41 also may be coated with hot melt adhesive and the segments of the first elastic elements 43 may be bonded without tension. It is also possible to deprive or restrict any contractibility of the first elastic elements 43 laid under tension in the first non-elasticized region 41 and thereby to define the first non-elasticized region 41.

As will be apparent from the foregoing description, "non-elasticized region" refers to the non-elasticized region in which the elastic elements are substantially absent or the non-elasticized region in which the elastic elements are present but contractibility thereof are deprived.

While not illustrated, reason for existence of the first non-elasticized region 41 is: (a) just as in the case of the invention disclosed by JP2006-525858T, a patch printed with a graphic is attached to the inner surface of the first non-elasticized region 41 so as to make the graphic to be seen through the first non-elasticized region 41 from the exterior, and/or (b) the absorbent panel 23 is protected against undesirable deformation such as gathers due to contraction of the first elastic elements 43. Particularly as for the reason for existence (a), the absence of the first elastic elements 43 in the first non-elasticized region 41 is preferable in order to make the graphic to be clearly visible.

Figure 8:
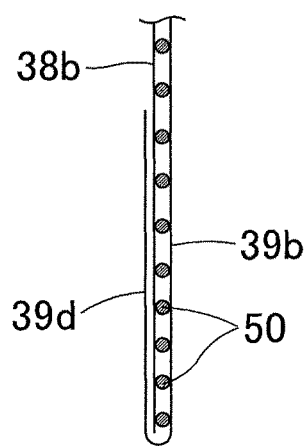
[FIG. 8] Schematic sectional view taken along the line VIII-VIII in FIG. 2.

Like the front waist panel 12A, the rear waist panel 12B is formed by a laminate of the inner sheet 38b and the outer sheet 39b. The outer sheet 39b has its dimension in the longitudinal direction larger than that of the inner sheet 38b and a prolongation 39d thereof is folded back onto the side of the inner sheet 38b (See FIG. 8) and bonded thereto by hot melt adhesive (not shown).

The rear waist panel 12B has transversely paired third elasticized regions 45 corresponding to the first elasticized regions 40 and opposed to each other in the transverse direction so as to be contractible in this direction, a fourth elasticized region 46 corresponding to portions of the first elasticized regions 40 and the second elasticized region 42 and lying adjacent to the side of the paired third elasticized regions 45 close to the waist-opening 18 (i.e., lower edges of the respective third elasticized regions 45 as viewed in FIG. 3), fifth elasticized regions 47 lying adjacent to the side of the paired third elasticized regions 45 close to the leg-openings 19 (i.e., upper edge of the paired third elasticized regions 45) and optionally a second non-elasticized region 48 corresponding to the first non-elasticized region 41 and extending between the paired third elasticized regions 45 as well as between the paired fifth elasticized regions 47. The fourth elasticized region 46 defines a rear waist band and cooperates with the front waist band to form the waist-opening 18. The third, fourth and fifth elasticized regions 45, 36, are elasticized to be contractible in the transverse direction by attaching a plurality of strand-like third, fourth and fifth elastic elements 49, 50, 51 under tension in the transverse direction between the inner and outer sheets 38a, 39a (See FIG. 5) by means of hot melt adhesive (not shown).

Pitches in the longitudinal direction at which the third and fourth elastic elements 49, 50 are set to be the same as those for the first and second elastic elements 43, 44. The pitch in the longitudinal direction at which the fifth elastic elements 51 are arranged is set to be larger than those for the first and third elastic elements 43, 49. Tensile stress of the third and fourth elasticized regions 45, 46 in the transverse direction is set to be the same as that of the first and second elasticized regions 40, 42 in the transverse direction. Tensile stress of the fifth elasticized region 47 in the transverse direction is set to be lower than that of the third elasticized region 45 in the transverse direction. The tensile stresses of the respective elasticized regions in the transverse direction are represented by a relational expression: the second elasticized region 42=the fourth elasticized region 46>the first elasticized regions 40=the third elasticized regions 45>the fifth elasticized regions 47. Alternatively, the first elasticized regions 40=the second elasticized region 42=the third elasticized regions 45=the fourth elasticized region 46>the fifth elasticized regions 47.

Now a method for measuring tensile stresses of the respective elasticized regions in the waist panel will be described. First, the front and rear waist regions are peeled off from each other along the seams and the diaper 10 is flatly developed as seen in FIG. 2 and the respective elastic elements are stretched to the maximum stretched length in the transverse direction. The entire waist panel 12A and the entire waist panel 12B are cut off from the diaper 10 and the respective elasticized regions are cut away from these waist panels 12A, 12B to obtain desired test pieces. Based on these test pieces, widths (dimensions in the longitudinal direction of the diaper 10) of the respective regions are measured. When the respective elasticized regions are cut off from the test pieces, the region defined between each pair of the adjacent elastic elements is cut along a longitudinal center line of this region. Then, each of the test pieces in a contracted state is fixed between a pair of chucks of Tensile Tester (manufactured by Shimadzu Corporation (a distance between these chucks is initially set to 100 mm and appropriately adjusted depending on the each of the test pieces). Now the test piece is stretched in the transverse direction of the diaper 10 at a rate of 100 mm/min and a load (mN) at 65% of the maximum stretched length is measured. Thus, tensile stress is calculated for each of the elasticized regions according to an equation:

Measured value (mN)÷region width (mm)=tensile stress. As for the elasticized regions in the side flaps and the barrier leg cuffs also, measurement may be carried out in the similar manner as has been described above.

In each of the fifth elasticized regions 47, the number of the fifth elastic elements 51 is fewer than the number of the first through fourth elastic elements 43, 44, 49, 50 and the tensile stress of the respective fifth elasticized regions 47 in the transverse direction is lower than those of the first through fourth elasticized regions 40, 42, 45, 46 as has previously been described in reference to the associated drawings. With this unique arrangement, the respective fifth elasticized regions 47 properly cover a desired area of the wearer's buttock when the diaper 10 is put on the wearer's body, forming a soft contact surface along a curve of the buttock. In addition, irregular frills should not appear and disfigure the appearance of the diaper 10 put on the wearer's body because none of the elastic elements is present along the oblique inner side edges 12g.

The number of the fifth elastic elements 51 is fewer than the number of the third elastic elements 49 and therefore the presence of these fifth elastic elements 51 should not deteriorate desired visibility of the graphic even when these fifth elastic elements 51 are continuous in the transverse direction. To further improve the soft contact, transversely opposite outer ends 51a of the fifth elastic elements 51 preferably terminate short of the oblique inner side edges 12g.

Referring again to FIG. 2, in each of the lateral regions of the fifth elasticized region 47 opposite in the transverse direction, an imaginary triangular region 47A having an apex A (i.e., the region contoured by chain double-dashed lines) is defined by a line defined by the elastic element 49' lying nearest to the crotch region 17 in the third elasticized region 45, a line defined by the outermost elastic element 33 in each of the side flaps 31 as viewed in the transverse direction and each of the inner side edges 12g of the fifth elasticized region 47. With the diaper 10 put on the wearer's body, respective triangular regions having apices are contracted in the longitudinal direction as well as in the transverse direction by cooperative contraction of the elastic element 49' in the third elasticized region 45, the outermost elastic elements 33 of the side flaps 31 and contraction of the fifth elasticized regions 47. In consequence, the respective triangular regions 47A are deformed substantially in cup-shapes and elastically brought in relatively soft contact with curved surface of the wearer's buttock.

As stock material for the inner and outer sheets 38a, 39a, 38b, 39b defining the front and rear waist panels 12A, 12B, a hydrophobic fibrous nonwoven fabric, a moisture-pervious plastic film or a laminate thereof is suitable. The other features of the rear waist panel 12B are the same as those of the front waist panel 12A.

Referring again to FIGS. 1, 2 and 3, the absorbent chassis 11 has its front end region 11d joined to the inner surface of the front waist panel 12A and its rear end region 11e joined to the inner surface of the rear waist panel 12B, in both cases, by hot melt adhesive or the other fastening means (not shown). The front and rear waist panels 12A, 12B are joined together along opposite side edges 12c of the front waist panel 12A and along opposite side edges 12f of the rear waist panel 12B to define the annular waist band.

The diaper 10 of such construction functions on the wearer's body in the manner as will be described. The annular waist panel 12 contracts in the transverse direction (i.e., circumferentially with respect to the waist) as the respective elastic elements 43, 44, 49, 50, 51 contract. Particularly, contraction of the first elastic elements 43 in the front waist panel 12A cooperates with contraction of the auxiliary elastic elements 37 to deform the lateral regions 20a of the absorbent structure 20 in the absorbent chassis 11 inward along the deformation guides 36 so that the lateral regions 20a rise in face-to-face relationship toward the wearer's crotch so as to form the absorbent barriers against body waste as exemplarily illustrated in FIG. 6. Thereupon, the side flaps 31 and the barrier leg cuffs 26 are also deformed inward in a face-to-face relationship under contraction of the elastic elements 33, 34, respectively. At the same time, the distal edges 26b of the paired barrier leg cuffs 26 and the side flaps 31 raise themselves toward the wearer's crotch. In this way, the lateral regions 20a of the absorbent structure 20 and the distal edges 26b of the paired barrier leg cuffs 26 raising themselves in this manner are elastically held in contact with the wearer's inguinal region so far as the diaper 10 is properly put on the wearer's body. Similarly, the side flaps 31 raising themselves also are elastically held in contact with the wearer's thighs.

The first elastic elements 43 associated with the front waist panel 12A lying adjacent the deformation guides 36 primarily contribute to said deformation of the lateral zones 20a in the absorbent structure 20 and similarly the auxiliary elastic elements 37 lying adjacent the deformation guides 36 cooperate with the first elastic elements 43 to assist said deformation. These elastic elements 43, 37 are preferably provided but not essential for the present invention.

The present invention can be exploited by employing the previously described "method of laterally oriented feeding mode". While the first through the fifth elastic elements 43, 44, 49, 50, 51 associated with the front and rear waist panels 12A, 12B, on one hand, and the elastic elements 33, 34, 37 associated with the absorbent chassis 11, on the other hand, are arranged to contract in the directions orthogonal to each other, both the elastic elements associated with the absorbent chassis and the elastic members associated with the front and rear waist panels are linearly fed in the machine direction. After the associated elastic elements have been attached to the absorbent chassis, the latter is turned by an angle of 90° and laminated on the front and rear waist panels. In this manner, all the elastic elements associated with the front and rear waist panels and the absorbent chassis are linearly fed and attached thereto.

The invention claimed is:

1. A disposable absorbent wearing article defining a longitudinal center line in a longitudinal direction and a transverse center line in a transverse direction, said disposable absorbent wearing article comprising;

an elasticized front waist panel and an elasticized rear waist panel respectively defining a front waist region and a rear waist region;

an absorbent chassis joined to and extending between said front and rear waist panels in said longitudinal direction, said absorbent chassis defining respective parts of said front and rear waist regions and defining a crotch region;

said absorbent chassis including an absorbent structure having an absorbent core and a pair of side flaps extending outward in said transverse direction from opposite lateral regions of said absorbent core, each of said pair of side flaps being elastically contractible under an effect of at least one strand of an elastic element attached thereto;

said front waist panel including a first elasticized region and a second elasticized region, said second elasticized region lying adjacent to said first elasticized region and defining a waist band;

said rear waist panel including a third elasticized region, a fourth elasticized region and a pair of fifth elasticized regions, said third elasticized region corresponding to said first elasticized region, said fourth elasticized region corresponding to said second elasticized region, said pair of fifth elasticized regions lying adjacent to said third elasticized region on a side thereof toward said crotch region; said third elasticized region and said fourth elasticized region being elastically contractible by a plurality of strands of elastic elements extending in said transverse direction;

said pair of fifth elasticized regions having inner side edges that are opposed to each other in said transverse direction, said inner side edges extending obliquely relative to said longitudinal center line, said pair of elasticized regions being elastically contractible by at least one strand of an elastic element;

said pair of fifth elasticized regions having a tensile stress in said transverse direction that is less than a tensile stress of any of said first, second, third and fourth elasticized regions; and said rear waist panel having a rear panel dimension measured in said longitudinal direction that is greater than a front panel dimension of said front waist panel measured in said longitudinal direction by a fifth region dimension of said fifth elasticized region measured in said longitudinal direction.

2. The wearing article according to claim 1, wherein a pair of triangles are defined opposite of one another in said transverse direction, each of said triangles being formed by a line defined by an elastic element located nearest to said crotch region in each of said pair of third elasticized regions, a line defined by an outermost elastic element located in each of said side flaps of said absorbent chassis and by said inner edge of said pair of fifth elasticized regions.

3. The wearing article according to claim 2, wherein said first and second elasticized regions include a plurality of strands of elastic elements extending in said transverse direction and are elastically contractible by an effect thereof.

4. The wearing article according to claim 3, wherein said inner side edges of said pair of fifth elasticized regions are concavely curved inward so as to define circular arcs.

5. The wearing article according to claim 2, wherein said inner side edges of said pair of fifth elasticized regions are concavely curved inward so as to define circular arcs.

6. The wearing article according to claim 2, wherein said at least one strand of elastic element in said pair of fifth elasticized regions extends short of said inner side edges.

7. The wearing article according to claim 2, wherein said front waist panel includes front side edges located generally opposite in said transverse direction of one another, wherein said rear waist panel includes rear side edges located generally opposed in said transverse direction of one another, said front side edges being joined to said rear side edges to form an annular waist panel defining a waist-opening and a pair of leg-openings.

8. The wearing article according to claim 1, wherein said first and second elasticized regions include a plurality of strands of elastic elements extending in said transverse direction and are elastically contractible by an effect thereof.

9. The wearing article according to claim 8, wherein said inner side edges of said pair of fifth elasticized regions are concavely curved inward so as to define circular arcs.

10. The wearing article according to claim 9, wherein said at least one strand of elastic element in said pair of fifth elasticized regions extends short of said inner side edges.

11. The wearing article according to claim 8, wherein said at least one strand of elastic element in said pair of fifth elasticized regions extends short of said inner side edges.

12. The wearing article according to claim 8, wherein said front waist panel includes front side edges located generally opposite in said transverse direction of one another, wherein said rear waist panel includes rear side edges located generally opposed in said transverse direction of one another, said front side edges being joined to said rear side edges to form an annular waist panel defining a waist-opening and a pair of leg-openings.

13. The wearing article according to claim 1, wherein said inner side edges of said pair of fifth elasticized regions are concavely curved inward so as to define circular arcs.

14. The wearing article according to claim 13, wherein said at least one strand of elastic element in said pair of fifth elasticized regions extends short of said inner side edges.

15. The wearing article according to claim 14, wherein said front waist panel includes front side edges located generally opposite in said transverse direction of one another, wherein said rear waist panel includes rear side edges located generally opposed in said transverse direction of one another, said front side edges being joined to said rear side edges to form an annular waist panel defining a waist-opening and a pair of leg-openings.

16. The wearing article according to claim 13, wherein said front waist panel includes front side edges located generally opposite in said transverse direction of one another, wherein said rear waist panel includes rear side edges located generally opposed in said transverse direction of one another, said front side edges being joined to said rear side edges to form an annular waist panel defining a waist-opening and a pair of leg-openings.

17. The wearing article according to claim 1, wherein said at least one strand of elastic element in said pair of fifth elasticized regions extends short of said inner side edges.

18. The wearing article according to claim 17, wherein said front waist panel includes front side edges located generally opposite in said transverse direction of one another, wherein said rear waist panel includes rear side edges located generally opposed in said transverse direction of one another, said front side edges being joined to said rear side edges to form an annular waist panel defining a waist-opening and a pair of leg-openings.

19. The wearing article according to claim 1, wherein said front waist panel includes front side edges located generally opposite in said transverse direction of one another, wherein said rear font waist panel includes rear side edges located generally opposed in said transverse direction of one another, said front side edges being joined to said rear side edges to form an annular waist panel defining a waist-opening and a pair of leg-openings.

* * * * *

UNITED STATES PATENT AND TRADEMARK OFFICE
CERTIFICATE OF CORRECTION

PATENT NO. : 8,518,010 B2 Page 1 of 1
APPLICATION NO. : 12/935706
DATED : August 27, 2013
INVENTOR(S) : Kuwano et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 356 days.

Signed and Sealed this
Fifteenth Day of September, 2015

Michelle K. Lee
*Director of the United States Patent and Trademark Office*